(12) United States Patent
Sankai

(10) Patent No.: US 12,249,150 B2
(45) Date of Patent: Mar. 11, 2025

(54) INSTRUMENT MONITORING DEVICE AND INSTRUMENT MONITORING METHOD

(71) Applicant: CYBERDYNE Inc., Ibaraki (JP)

(72) Inventor: Yoshiyuki Sankai, Ibaraki (JP)

(73) Assignee: CYBERDYNE Inc., Ibaraki (JP)

( * ) Notice: Subject to any disclaimer, the term of this patent is extended or adjusted under 35 U.S.C. 154(b) by 553 days.

(21) Appl. No.: 17/776,957

(22) PCT Filed: Nov. 24, 2020

(86) PCT No.: PCT/JP2020/043627
§ 371 (c)(1),
(2) Date: May 13, 2022

(87) PCT Pub. No.: WO2021/106859
PCT Pub. Date: Jun. 3, 2021

(65) Prior Publication Data
US 2022/0392227 A1 Dec. 8, 2022

(30) Foreign Application Priority Data

Nov. 25, 2019 (JP) .................. 2019-212107

(51) Int. Cl.
*G06V 20/52* (2022.01)
*G06T 7/20* (2017.01)
(Continued)

(52) U.S. Cl.
CPC ................ *G06V 20/52* (2022.01); *G06T 7/20* (2013.01); *G06T 7/70* (2017.01); *G06V 20/60* (2022.01);
(Continued)

(58) Field of Classification Search
CPC .. G06V 20/52; G06V 20/20; G06V 2201/034; G06V 20/40; G06V 20/41;
(Continued)

(56) References Cited

U.S. PATENT DOCUMENTS

| 2003/0192722 A1* | 10/2003 | Ballard .............. G01G 23/3735 |
| | | 177/25.19 |
| 2007/0268133 A1* | 11/2007 | Sanchez ............. G08B 13/2462 |
| | | 340/568.1 |

(Continued)

FOREIGN PATENT DOCUMENTS

JP 2019-500921 A 1/2019

OTHER PUBLICATIONS

Patent Cooperation Treaty, International Search Report, Application No. PCT/JP2020/043627, dated Dec. 23, 2020, in 7 pages.

*Primary Examiner* — Ajibola A Akinyemi
(74) *Attorney, Agent, or Firm* — Procopio, Cory, Hargreaves & Savitch LLP

(57) ABSTRACT

It is judged that a relevant tool is lost at a second time point after the elapse of a certain amount of time or longer after a first time point when it is judged that the tool is not recognized at all in images; and regarding the tool which is judged to have been lost, trace data corresponding to heads-up time, which is immediately before the first time point to immediately after the first time point, is read with reference to a corresponding identifier and a movement locus of the tool based on the trace data is displayed on a screen.

12 Claims, 5 Drawing Sheets

1 NEEDLE MONITORING APPARATUS

(51) Int. Cl.
  *G06T 7/70*      (2017.01)
  *G06V 20/60*     (2022.01)
  *G10L 15/22*     (2006.01)
(52) U.S. Cl.
  CPC .... *G10L 15/22* (2013.01); *G06T 2207/30004* (2013.01); *G06T 2207/30232* (2013.01); *G06V 2201/034* (2022.01)
(58) Field of Classification Search
  CPC ........ G06V 20/44; G06V 20/49; G06V 40/10; G06V 40/20; G06V 40/174; G06V 10/145; G06V 10/25; G06V 40/107; G06V 10/34; G06V 10/50; G06V 10/56; G06V 10/82; G06V 20/10; G06V 20/56; G06V 40/167; G06V 40/176; G06V 40/28; G06V 10/454; G06V 10/95
  USPC ........................................................ 382/128
  See application file for complete search history.

(56) References Cited

U.S. PATENT DOCUMENTS

| | | | | |
|---|---|---|---|---|
| 2009/0317002 A1* | 12/2009 | Dein | ...................... | A61B 50/20 340/568.1 |
| 2011/0163854 A1* | 7/2011 | Hamelin | ................ | A61B 90/96 235/491 |
| 2019/0006047 A1 | 1/2019 | Gorek et al. | | |

\* cited by examiner

FIG. 2
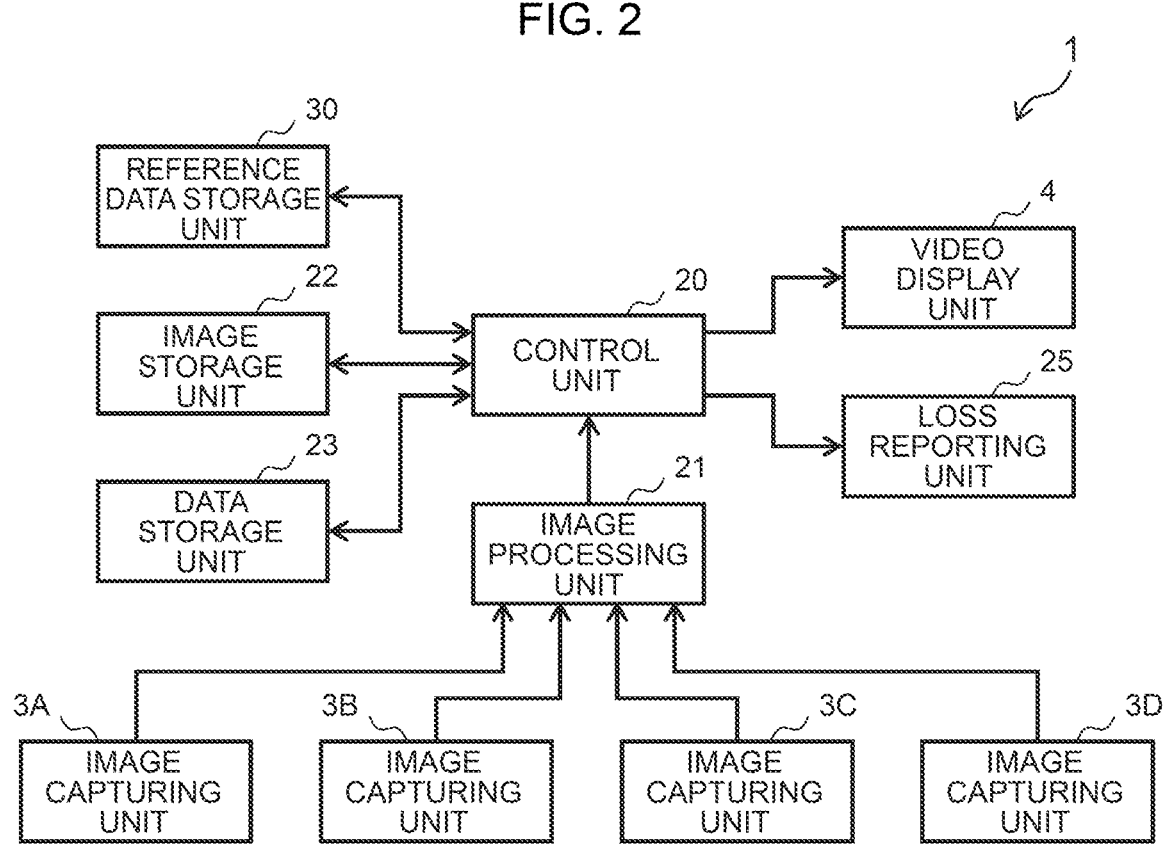
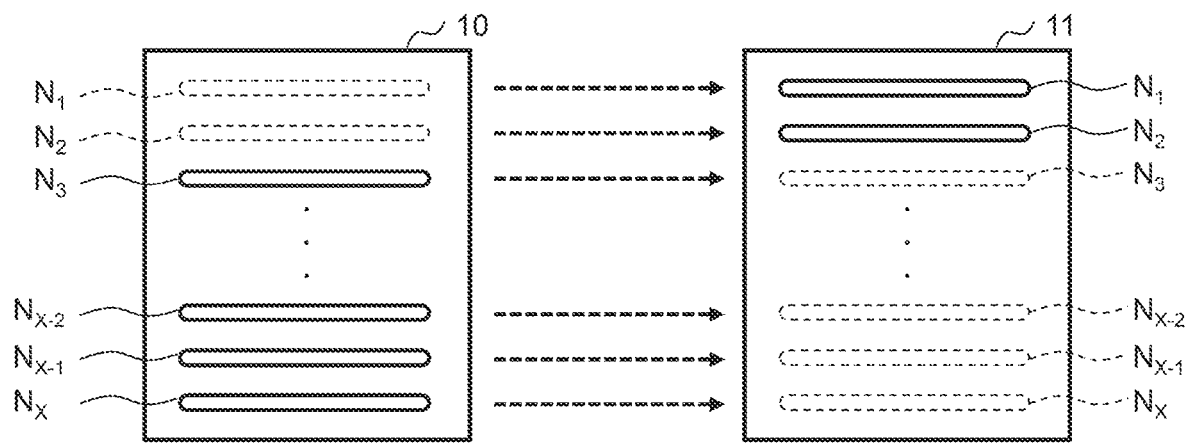

FIG. 5
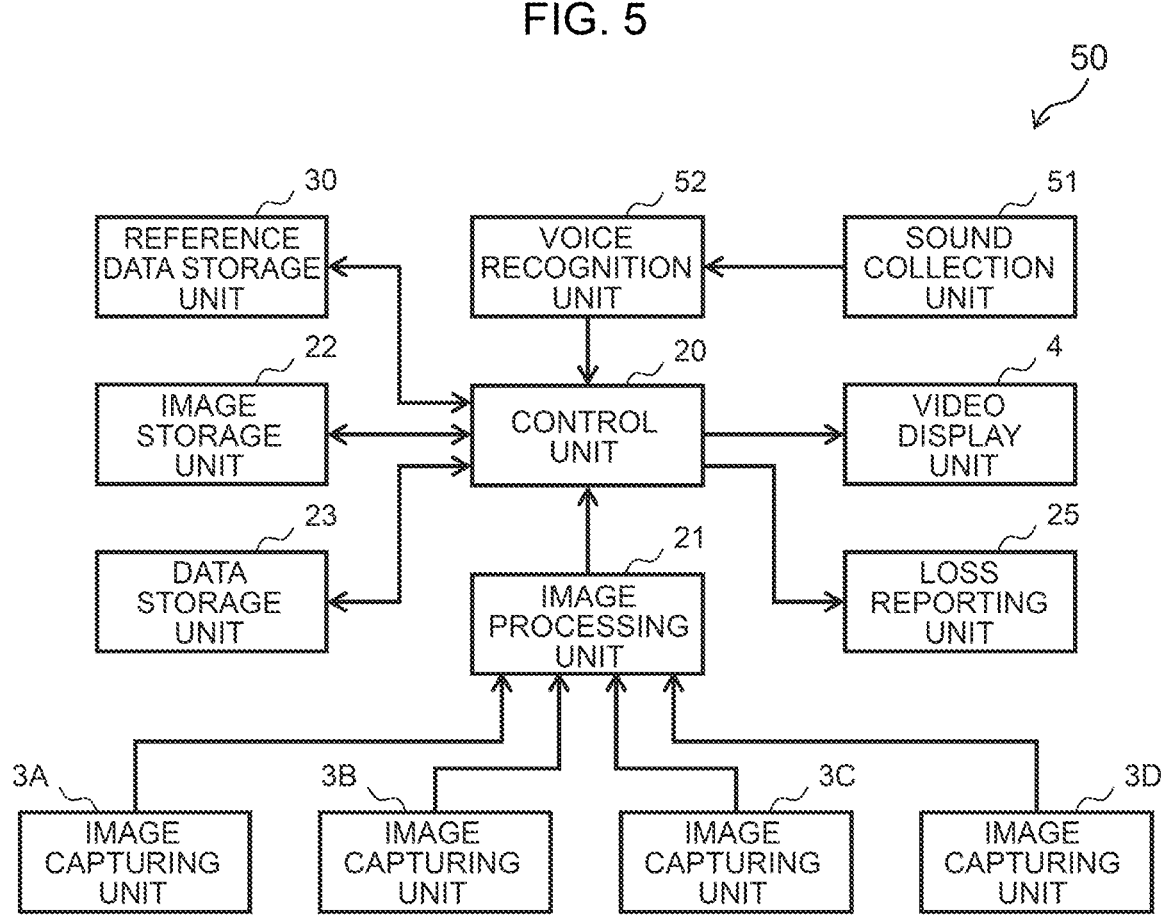
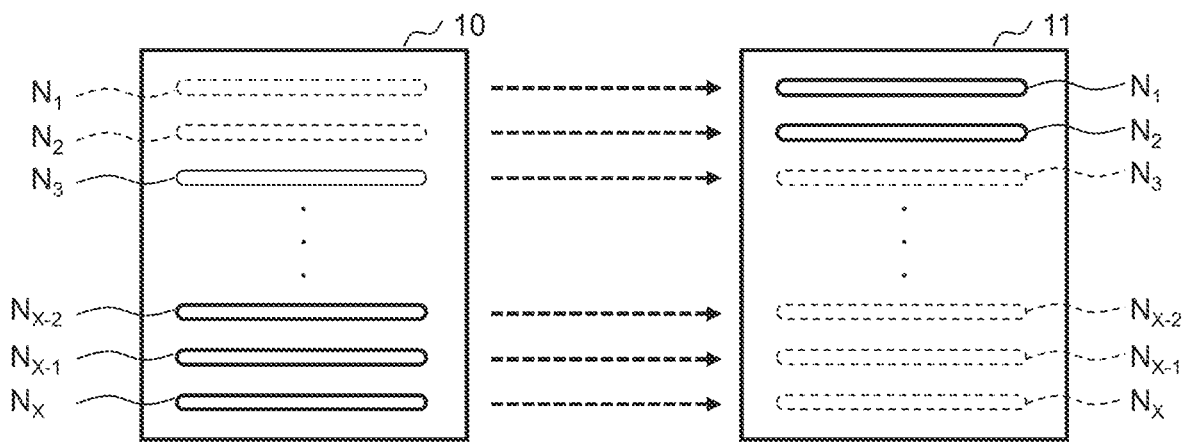

INSTRUMENT MONITORING DEVICE AND INSTRUMENT MONITORING METHOD

CROSS-REFERENCE TO RELATED APPLICATIONS

This application is US National Stage of International Patent Application PCT/JP2020/043627, filed Nov. 24, 2020, which claims benefit of priority from Japanese Patent Application JP2019-212107, filed Nov. 25, 2019, the contents of both of which are incorporated herein by reference.

TECHNICAL FIELD

The present invention relates to a tool monitoring apparatus and a tool monitoring method and is suited for application to a tool monitoring apparatus and tool monitoring method for preventing the loss of minute tools such as surgical needles used in surgical operations.

BACKGROUND ART

Conventionally, when a doctor performs a surgical operation on a patient in an operating room, there have been cases of accidents where surgical operation tools such as a surgical needle(s), a scalpel, or forceps are left inside the patient's body. Particularly, in a case of minute surgical tools such as the surgical needles, it is desirable that each of a plurality of surgical needles should be always monitored to prevent the loss of each surgical needle after each surgical needle is sequentially extracted from a needle holder, in which the plurality of surgical needles are retained, until each of them is housed in a needle counter.

Conventionally, there has been proposed a system for tracking the use of various surgical operation tools through the entire sequence of procedures by a doctor in an operating room (see PTL 1). This system is designed to capture data related to distribution and housing of surgical needles in the entire sequence of procedures by the doctor and manage time required to move a plurality of surgical needles, which are taken out of a suture pack, into a needle receiver.

CITATION LIST

Patent Literature

PTL 1: Japanese Unexamined Patent Application Publication (Translation of PCT Application) No. 2019-500921

SUMMARY OF THE INVENTION

Problems to be Solved by the Invention

Meanwhile, PTL 1 is a method of tracking and comparing the number of distributed surgical needles with the number of housed surgical needles and can automatically count all the surgical needles in the operating room; however, it is only possible to judge whether any surgical needle(s) has been finally lost or not.

Therefore, there is a problem such that it is very difficult for the doctor who is performing the surgical operation at which point of time during the surgical operation which surgical needle got lost at which location inside the operating room.

The present invention was devised in consideration of the above-described circumstances and aims at proposing a tool monitoring apparatus and tool monitoring method capable of always monitoring each of the plurality of tools during a period of time after the plurality of tools to be handled by a worker in a workroom are sequentially extracted until they are housed.

Means to Solve the Problems

In order to solve the above-described problem, there is provided according to the present invention a tool monitoring apparatus for monitoring each of a plurality of tools when a worker performs specified work on an object in a workroom and while each tool is sequentially extracted from a tool holder, in which the plurality of tools are retained, until each tool is housed in a tool counter, wherein the tool monitoring apparatus includes: a plurality of image capturing units that capture images centered on an area around hands of the worker and the object inside the workroom from multiple directions; an image recognition unit that recognizes each of the tools, which moves within an image capture range of the plurality of the image capturing units, in the images with respect to each of the image capturing units while assigning an identifier to each of the tools in an order of extraction from the tool holder; a movement locus storage unit that stores trace data indicating a movement locus of each tool by associating the trace data with the identifier corresponding thereto, while tracking a moving position of each tool for each of the image capturing units with respect to each tool recognized in the images by the image recognition unit; a loss judgment unit that judges that the tool is lost, at a second time point after an elapse of a certain amount of time or longer after a first time point when it is judged that the tool is not recognized at all in the images by the image recognition unit, with respect to each of the tools regarding which the trace data is stored by the movement locus storage unit; and a movement locus display unit that displays the movement locus of the tool based on the trace data on a screen, with respect to the tool which is judged by the loss judgment unit to have been lost, by reading the trace data corresponding to heads-up time, which is from immediately before the first time point to immediately after the first time point, from the movement locus storage unit with reference to the corresponding identifier.

As a result, when the worker sequentially extracts and handles the plurality of tools, the tool monitoring apparatus can present the status before and after the loss of a tool which may highly possibly have been lost to the worker by displaying images of the movement locus of the relevant tool from immediately before the first time point to immediately after the first time point at the second time point when it is judged that the tool is lost.

Also, the tool monitoring apparatus according to the present invention includes: a sound collection unit that collects ambient sounds of the worker; and a voice recognition unit that extracts and recognizes specified utterance content regarding the tool among utterances of the worker from the ambient sounds collected by the sound collection unit, wherein when the loss judgment unit receives a recognition result of the utterance content regarding the tool from the voice recognition unit during a period of time from the first time point to the second time point, the loss judgment unit judges that the tool is lost, even before the second time point passes. As a result, the tool monitoring apparatus can prevent the occurrence of problems attributable to the loss of the relevant tool by immediately dealing with the loss at the time point when the worker recognizes the loss of the tool.

Moreover, according to the present invention, the movement locus display unit displays the movement locus of the tool, which is judged by the loss judgment unit to have been lost, on the screen by switching to each of the image capturing units on the basis of the heads-up time. As a result, with the tool monitoring apparatus, the worker can check, with respect to each relevant image capturing unit, in which image capture range by which image capturing unit the tool which may highly possibly have been finally lost is included.

Furthermore, according to the present invention, the movement locus display unit repeatedly displays the movement locus of the tool by the image capturing unit designated by the worker on the screen on the basis of the heads-up time. As a result, with the tool monitoring apparatus, the worker can visually check the captured image content of the tool, which may highly possibly have been finally lost, many times on the basis of repetitions from immediately before the first time point to immediately after the first time point.

Furthermore, according to the present invention, the tool monitoring apparatus includes a loss reporting unit that reports a possibility of loss of the relevant tool, by means of either one of, or both, a voice and a light emission, to the worker at the first time point when the loss judgment unit judges that the tool is not recognized at all in the images by the image recognition unit. As a result, with the tool monitoring apparatus, the worker can check whether the relevant tool exists or not during the work by receiving a notice reporting the possibility of loss of the tool at the first time point when it is judged that the tool may highly possibly have been lost.

Furthermore, according to the present invention, when the loss judgment unit judges that, with respect to each of the tools regarding which the trace data is stored by the movement locus storage unit, the tool is not housed in the tool counter after the work is finished, the loss judgment unit judges that the tool is lost. As a result, with the tool monitoring apparatus, the worker can check whether any tool which is not housed in the tool counter exists.

Furthermore, there is provided according to the present invention a tool monitoring method for monitoring each of a plurality of tools when a worker performs specified work on an object in a workroom and while each tool is sequentially extracted from a tool holder, in which the plurality of tools are retained, until each tool is housed in a tool counter, wherein the tool monitoring method includes: a first step causing a plurality of image capturing units to capture images centered on an area around hands of the worker and the object inside the workroom from multiple directions and recognizing each of the tools, which moves within an image capture range of each of the plurality of the image capturing units, in the images while assigning an identifier to each of the tools in an order of extraction from the tool holder; a second step of storing trace data indicating a movement locus of each tool by associating the trace data with the identifier corresponding thereto, while tracking a moving position of each tool for each of the image capturing units with respect to each tool recognized in the images in the first step; a third step of judging that the tool is lost, at a second time point after an elapse of a certain amount of time or longer after a first time point when it is judged that the tool is not recognized at all in the images in the first step, with respect to each of the tools regarding which the trace data is stored by the second step; and a fourth step of displaying the movement locus of the tool based on the trace data on a screen, with respect to the tool which is judged by the third step to have been lost, by reading the trace data corresponding to heads-up time, which is from immediately before the first time point to immediately after the first time point, with reference to the corresponding identifier.

As a result, when the worker sequentially extracts and handles the plurality of tools, the tool monitoring method can present the status before and after the loss of a tool which may highly possibly be lost to the worker by displaying images of the movement locus of the relevant tool from immediately before the first time point to immediately after the first time point at the second time point when it is judged that the tool is lost.

Advantageous Effects of the Invention

According to the present invention, it is impossible to implement the tool monitoring apparatus and tool monitoring method capable of solving the loss problem at an early stage while always monitoring the plurality of tools handled by the worker inside the workroom.

BRIEF DESCRIPTION OF DRAWINGS

FIG. 2 is a block diagram illustrating a circuit configuration of the needle monitoring apparatus according to this embodiment;

FIG. 5 is a block diagram illustrating a circuit configuration of a needle monitoring apparatus according to another embodiment.

DESCRIPTION OF EMBODIMENTS

An embodiment of the present invention will be described below in detail with reference to the drawings.

Figure 1:
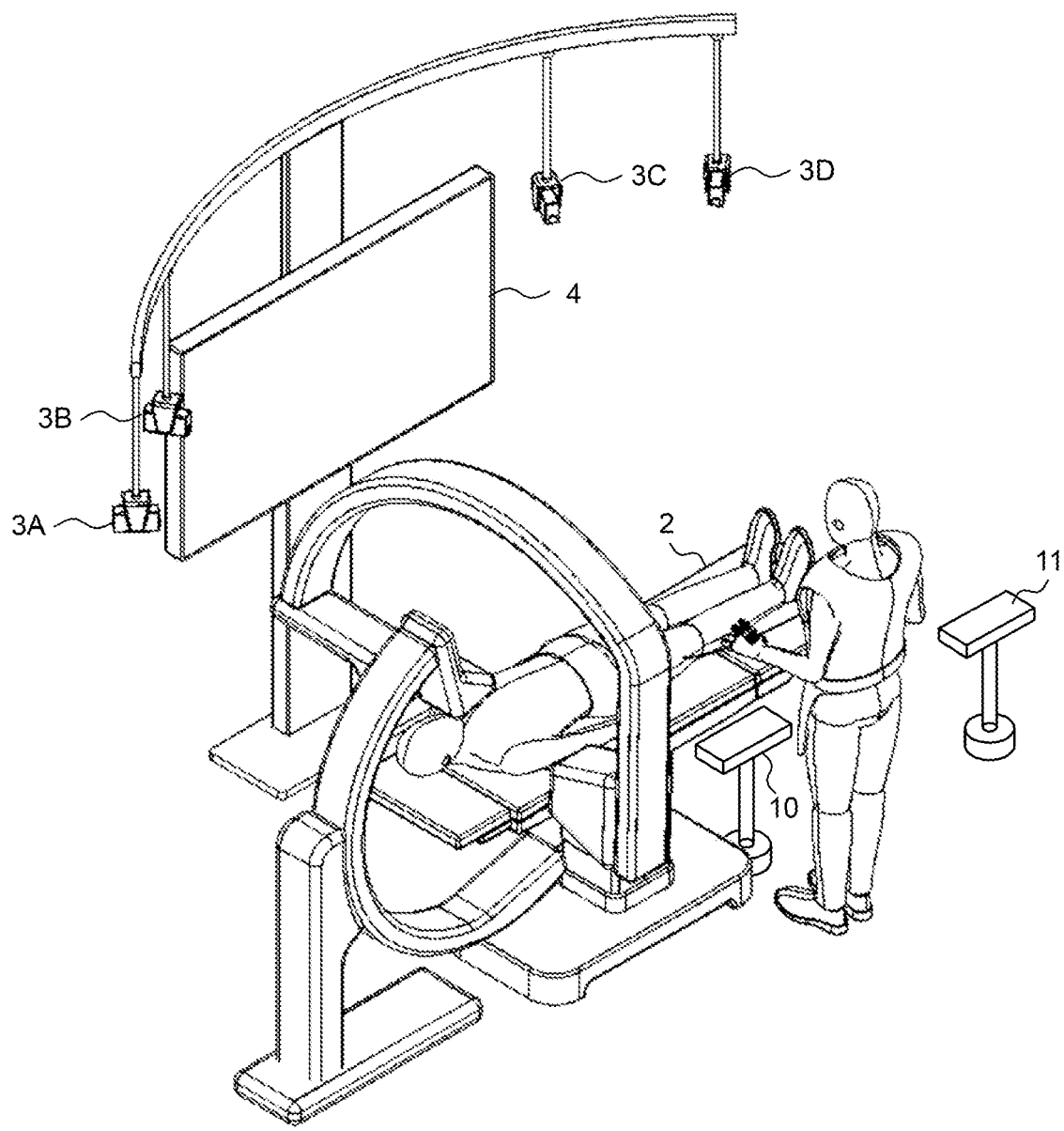
FIG. 1 is a schematic conceptual diagram illustrating one example of a usage form of a needle monitoring apparatus according to an embodiment of the present invention.

(1) An Example of Usage Form of Needle Monitoring Apparatus According to this Embodiment FIG. 1 and FIG. 2 illustrate a needle monitoring apparatus 1 according to this embodiment as a whole, which is designed so that when a doctor performs a surgical operation on a patient who is lying on an operating table 2 in an operating room, a plurality of image capturing units 3A to 3D which are composed of CMOS image sensors capture images centered on an area around the doctor's hands and the patient inside the operating room from multiple directions.

The needle monitoring apparatus 1 has a video display unit 4 equipped with a video display and a speaker, so that it displays, on the video display, a data group video indicating various data such as an electrocardiogram detected from the patient during the surgical operation and, at the same time, generates voices accompanying the video from the speaker.

The needle monitoring apparatus 1 includes: a needle holder 10 in which a plurality of surgical needles $N_1$ to $N_X$ are retained; and a needle counter 12 from which the respective surgical needles $N_1$ to $N_X$ are sequentially extracted and in which they are housed.

The needle monitoring apparatus 1 includes: a control unit 20 configured from a CPU (Central Processing Unit) which integrally controls the entire apparatus; an image processing unit 21 which processes each of image capture results by the plurality of image capturing units 3A to 3D as image data; and an image storage unit 22 which is configured from, for example, an SSD(s) (Solid State Drive(s)) and stores the image data of each image capturing unit 3A to 3D by the image processing unit 21.

The control unit 20 recognizes each surgical needle $N_1$ to $N_X$, which moves within an image capture range of each image capturing unit 3A to 3D, in images on the basis of image data of each frame image according to each image capturing unit 3A to 3D, which is read from the image storage unit 22, while assigning ID numbers (identifiers) to the surgical needles $N_1$ to $N_X$ in the order extracted from the needle holder 10.

Then, the control unit 20 stores trace data indicating a movement locus of each surgical needle $N_1$ to $N_X$ in a data storage unit (movement locus storage unit) 23 with respect to each surgical needle $N_1$ to $N_X$ recognized in the images by associating the trace data with the corresponding ID number, while tracking the moving position of each surgical needle $N_1$ to $N_X$ with respect to each image capturing unit 3A to 3D.

Regarding each surgical needle $N_1$ to $N_X$ whose trace data is stored by the data storage unit 22, the control unit 20 judges that the surgical needle $N_1$ to $N_X$ is lost, at a second time point after the elapse of a certain amount of time or longer after a first time point where it is judged based on the image data for each image capturing unit 3A to 3D that the relevant the surgical needle $N_1$ to $N_X$ is not recognized at all in the images.

Regarding the surgical needle $N_1$ to $N_X$ which is judged to have been lost, the control unit 20 reads the trace data corresponding to heads-up time, which is from immediately before the first time point to immediately after the first time point, from the data storage unit 23 with reference to the corresponding ID number and causes the movement locus of the surgical needle $N_1$ to $N_X$ based on the trace data to be displayed on the screen of the video display unit 4.

Incidentally, the needle monitoring apparatus 1 may include a loss reporting unit 25 that reports the possibility of loss of the relevant surgical needle $N_K$ to the doctor, by means of either one of, or both, a voice and a light emission, at the first time point where the control unit 20 judges that each surgical needle $N_1$ to $N_X$ is not recognized at all in the images. This loss reporting unit 25 is equipped with, for example, an LED lamp and a speaker and is designed to output preset light emission patterns and voice content according to control of the control unit 20.

Furthermore, the needle monitoring apparatus 1 is designed to judge that the relevant surgical needle is lost, when it is judged regarding the surgical needle $N_1$ to $N_X$ whose trace data is stored in the data storage unit 23 that the relevant surgical needle is not housed in the needle counter 11 after the surgical operation. As a result, with the needle monitoring apparatus 1, the doctor can check if any surgical needle which is not housed in the needle counter 11 exists.

(2) Method for Recognizing Each Surgical Needle in Images

The control unit 20 detects each of the plurality of surgical needles $N_1$ to $N_X$, which are moved from the needle holder 10 to the needle counter 11, on the basis of each piece of the image data acquired from the plurality of image capturing units 3A to 3D. As a precondition to such detection, images of all types and sizes which may possibly be used are registered as a database in a reference data storage unit 30 in advance with respect to the surgical needles $N_1$ to $N_X$ which are image recognition objects.

Specifically speaking, images of the surgical needles of all the types and sizes, which become registration objects, are captured from every angle directions in a three-dimensional space and the needle images are stored as reference data in the reference data storage unit 30 and registered as a database so as to clarify appearance shapes and sizes.

Practically, the surgical needles are classified based on their top end shapes such as round needles, reverse cutting needles, conventional cutting needles, side cutting spatula needles, taper cutting point needles, and blunt needles, and are also classified based on their body shapes such as straight needles, fishhook needles, bent tip needles, and curved needles (slightly curved, medium curved, highly curved, and very highly curved), for the purpose of guiding a suture thread precisely and smoothly. Moreover, the surgical needles are classified based on holes for the suture thread to pass through, such as spring holes and normal holes. Accordingly, the surgical needles have various combinations of their top end shapes, body shapes, and holes depending on surgical operation objects and have various sizes (entire length) according to symptoms of the surgical operation objects.

Figure 3:
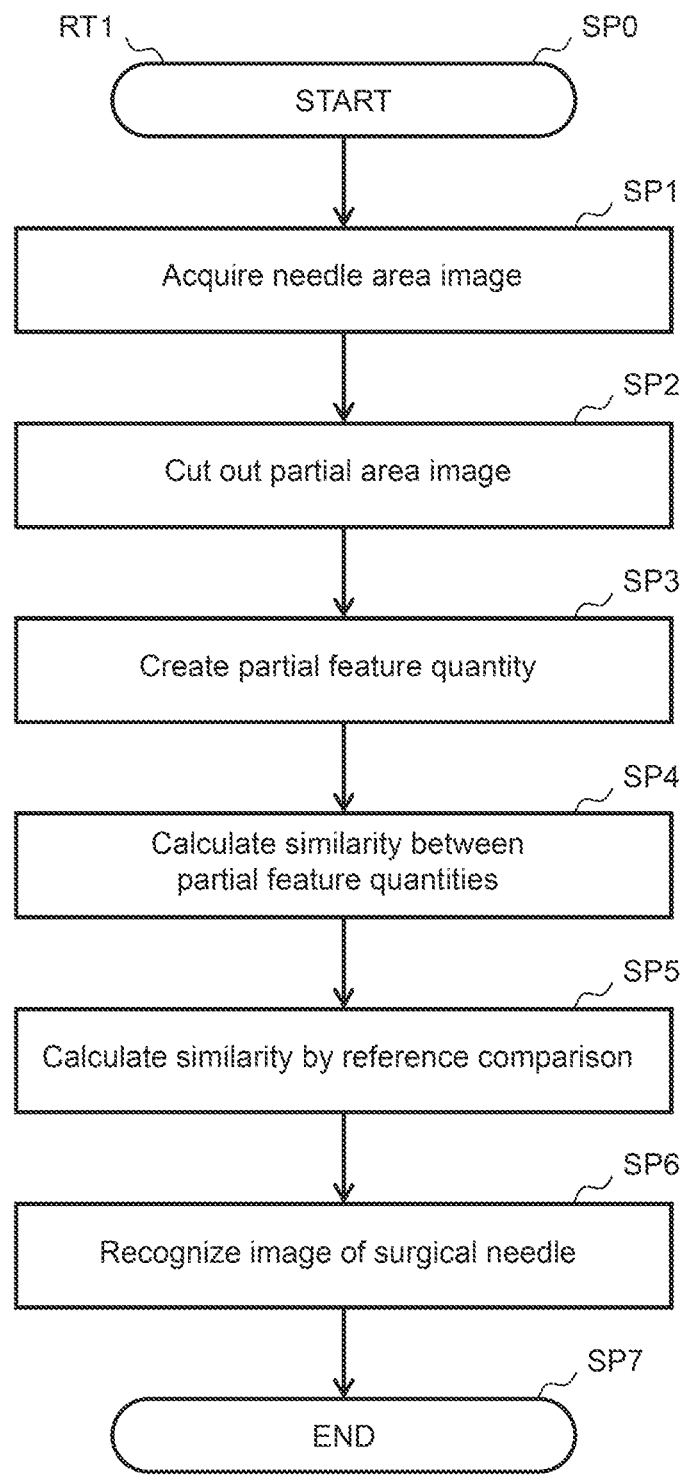
FIG. 3 is a flowchart illustrating an image recognition processing procedure according to this embodiment.

FIG. 3 illustrates a flowchart indicating image recognition processing of each surgical needle $N_1$ to $N_X$. After the doctor picks up a desired surgical needle $N_K$ (K is an arbitrary number from 1 to N) by using tweezers from the plurality of surgical needles $N_1$ to $N_X$ retained in the needle holder 10, the control unit 20 starts an image recognition processing procedure RT1 from step SP0 and detects the surgical needle $N_K$ in images from image capture results by the plurality of image capturing units 3A to 3D (step SP1).

The control unit 20 acquires a needle area image including the surgical needle $N_K$ from the captured images; however, since an image size of the needle area changes according to the distances to, and angles relative to, the image capturing units 3A to 3D, variable magnification processing is executed to adjust to the set image size.

When this happens, the control unit 20 may display a needle area frame superimposed the image of the surgical needle $N_K$ on a display screen displayed on the video display of the video display unit 4.

The control unit 20 detects a plurality of end points of constituent elements (the top end shape, the body shape, and the hole) of the relevant surgical needle $N_K$ as feature points from the needle area image including the surgical needle $N_K$ and cuts out a specified rectangular image (for example, a 5×5 pixel unit), as a partial area image, from the needle area image on the basis of a relative geometrical positional relationship with each feature point (step SP2).

Incidentally, the feature point may be obtained, for example, by extracting pixels with large differences from neighboring pixels, or by extracting pixels with many high frequency components obtained by multiplying the image data by FFT (Fast Fourier transform), or by extracting pixels by other methods.

The control unit 20 creates 25-dimensional (5×5 mesh) feature vectors and recognizes them as partial feature quantities on the basis of an edge-direction gradient histogram indicating a luminance value and edges extracted from the partial area image and stores the partial feature quantities in the reference data storage unit 30 (step SP3). Incidentally, for example, a Gabor Jet, Haar Wavelett, Gaussian Derivatives, and SIFT features may be used as the partial feature quantities.

The control unit 20 calculates respective similarities between all combinations of the partial feature quantities stored in the reference data storage unit 30 and stores them as a similarity distribution of the partial feature quantities in the reference data storage unit 30 (step SP4). When doing so, the control unit 20 executes similarity calculation processing by using an Euclidean distance, a Mahalanobis distance, and so on as scales for the similarities between the partial feature quantities.

For example, assuming that a partial area for recognizing the surgical needle $N_K$ is a P area and the number of feature quantities of the surgical needle $N_K$ registered in the reference data storage unit 30 for each partial area is Q, the control unit 20 calculates the similarities in a quantity of P×Q.

The control unit 20 finds similarity between the input image data of the surgical needle $N_K$ and the reference data from the similarities stored in the reference data storage unit 30 (step SP5). Firstly, the control unit 20 selects the highest similarity value, among the similarities calculated for each partial area, as the similarity representing the relevant partial area. Subsequently, the control unit 20 finds a total sum of the highest similarities of the respective partial areas in all the partial areas and outputs it as the similarity between the input image data of the surgical needle and the reference data.

The control unit 20: compares the similarity between the input image data of the surgical needle $N_K$ based on the found similarity and the reference data of the surgical needle $N_K$ which are stored in the reference data storage unit 30 and are classified according to the plurality of types and sizes; and recognizes a surgical needle of the type and size corresponding to the reference data, whose compared similarity becomes the highest, as the surgical needle $N_K$ corresponding to the input image data by using, for example, a group discrimination method implemented by statistical means such as a support vector machine and a kernel nonlinear discriminant analysis method (step SP6). Subsequently, the control unit 20 proceeds to step SP7 and terminates the image recognition processing procedure RT1.

Consequently, the control unit 20 can recognize each surgical needle $N_1$ to $N_X$ in images by extracting feature points respectively from images of the surgical needles $N_1$ to $N_X$ included in each image data acquired from the plurality of image capturing units 3A to 3D and images of the surgical needles according to the previously registered reference data and comparing and matching between the partial feature quantities surrounding them.

(3) Method for Tracking Each Surgical Needle

Figure 4:
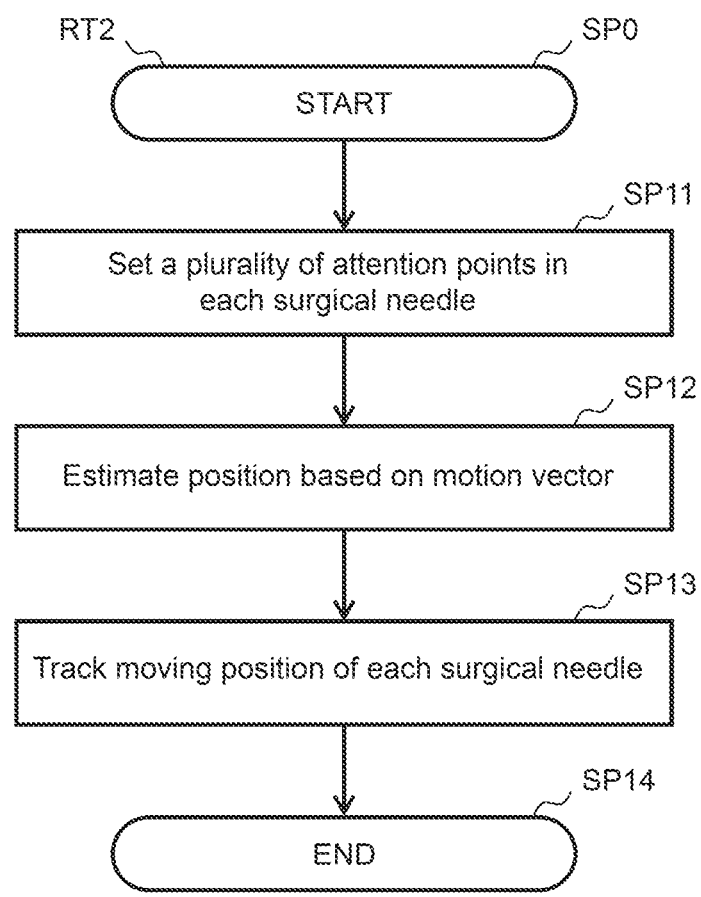
FIG. 4 is a flowchart illustrating a tracking processing procedure according to this embodiment.

FIG. 4 illustrates a flowchart indicating processing for tracking each surgical needle N1 to NX. The control unit 20 starts a tracking processing procedure RT2 from step SP10 following the above-described image recognition processing procedure RT1 and sets a plurality of attention points to each surgical needle $N_1$ to $N_X$ recognized in the images with respect to each image capturing unit 3A to 3D regarding the captured images respectively obtained from the plurality of image capturing units 3A to 3D (step SP11).

Then, regarding each attention point within the captured images of different image capture time points, the control unit 20 estimates the position of each attention point, which is set to a previous frame image, in a later frame image (a moving direction and a movement amount) on the basis of a motion vector calculated by a comparison between the frame images captured previously and later chronologically (step SP12).

Incidentally, the previous frame image and the later frame image do not have to be the images having the relationship of one of the images immediately before or immediately after the other, but may be any frame images among several previous and later frames. Furthermore, the motion vector may be calculated by means of, for example, block matching or a gradient method.

Subsequently, the control unit 20 tracks the moving position of each surgical needle $N_1$ to $N_X$ with respect to each image capturing unit 3A to 3D by analyzing motion vectors which are sequentially calculated in chronological order (step SP13). Specifically, the control unit 20 forms a histogram of the moving direction and speed (the movement amount) of each attention point, which is set to each surgical needle $N_1$ to $N_X$, on the basis of the relevant motion vector and analyzes a speed direction and a speed distribution, thereby judging whether each surgical needle exists in the captured image or not.

Incidentally, upon the analysis processing, a time series graph, two-dimensional mapping, a radar chart, and so on other than the histogram may be selected as appropriate according to movement properties which need to be analyzed. Subsequently, the control unit 20 proceeds to step SP13 and terminates the tracking processing procedure RT2.

Consequently, while tracking the moving position of each surgical needle $N_1$ to $N_X$ with respect to each image capturing unit 3A to 3D, the control unit 20 associates trace data indicating the movement locus of each surgical needle $N_1$ to $N_X$ with the corresponding ID number and stores them in the data storage unit 23.

(4) How to Handle Processing when Each Surgical Needle is Lost

The control unit 20 judges that the surgical needle $N_1$ to $N_X$ is lost, at the second time point after the elapse of a certain amount of time or longer after the first time point when it is judged that each surgical needle $N_1$ to $N_X$ whose trace data is stored by the data storage unit 23 is not recognized at all in the images on the basis of the image data for each image capturing unit 3A to 3D.

The certain amount of time from the first time point to the second time point is set within the range from several seconds to several tens of seconds; however, the doctor may freely set the time according to their own skills, etc..

The control unit 20: reads the trace data corresponding to heads-up time, which is from immediately before the first time point to immediately after the first time point, from the data storage unit 23 with reference to the corresponding ID number with respect to the surgical needle $N_1$ to $N_X$ which is judged to have been lost; and displays the movement locus of the surgical needle $N_1$ to $N_X$ based on the trace data on a screen of the video display of the video display unit 4.

As a result, when the doctor sequentially extracts and handles the plurality of surgical needles $N_1$ to $N_X$, the needle monitoring apparatus 1 presents the status before and after the loss of a tool, which may highly possibly have been lost, to the worker by displaying images of the movement locus of the relevant surgical needle $N_K$ from immediately before the first time point to immediately after the first time point, at the second time point when it is judged that the needle is lost.

(5) Other Embodiments

Incidentally, this aforementioned embodiment has described the case where when a doctor performs a surgical operation on a patient in an operating room, the needle monitoring apparatus 1 which monitors each surgical needle $N_1$ to $N_X$ while each surgical needle $N_1$ to $N_X$ is sequentially extracted from the needle holder 10, in which the plurality of surgical needles $N_1$ to $N_X$ are retained, until each of the surgical needles is housed in the needle counter 11, is applied as the tool monitoring apparatus according to the present invention; however, the present invention is not limited to this example and other surgical operation tools such as a scalpel or forceps, other than the surgical needles $N_1$ to $N_X$, may be applied.

Furthermore, as long as the tool monitoring apparatus is an apparatus which monitors each tool when a worker performs specified work on an object in a workroom and while each tool is sequentially extracted from a tool holder, in which a plurality of tools are retained, until each of the tools is housed in a tool counter, the tool monitoring apparatus can be widely applied to production lines such as assembling of components conveyance, maintenance work of automobiles, aircrafts, etc., and various precision work.

Moreover, this embodiment has described the case where four image capturing units are installed as the plurality of image capturing units 3A to 3D for capturing images centered on the area around hands of the doctor (worker) and the patient (object) inside the operating room (workroom) from multiple directions; however, the number of the image capturing units may be two or three, or five or more, and the desired number of the image capturing units may be installed depending on the situations at that time such as working conditions of the doctor (worker) or the number of the surgical needles (tools).

Furthermore, this embodiment has described the case where the image recognition unit that recognizes each surgical needle (tool) $N_1$ to $N_X$, which moves within the image capture range of the plurality of image capturing units 3A to 3D, in images with respect to each image capturing unit 3A to 3D while assigning identifiers to the surgical needles in the order extracted from the needle holder (tool holder) 10 is configured from the control unit 20 and the image processing unit 21; however, the present invention is not limited to this example and the image processing unit 21 may be provided for each image capturing unit 3A to 3D and the image recognition function may be provided as a separate circuit from the control unit 20.

Furthermore, this embodiment has described the case where the loss judgment unit which judges that the relevant tool is lost, at the second time point after the elapse of a certain amount of time or longer after the first time point where it is judged regarding each surgical needle (tool) $N_1$ to $N_X$, whose trace data is stored by the data storage unit (movement locus storage unit) 23, that the relevant surgical needle is not recognized at all in the images is executed by the control unit 20; however, the present invention is not limited to this example and the loss judgment unit may be executed by providing a separate circuit from the control unit 20.

Furthermore, in FIG. 5 indicating parts corresponding to the parts in FIG. 2 by assigning the same reference numerals as those in FIG. 2 to those corresponding parts, a needle monitoring apparatus 50 includes: a sound collection unit 51 composed of a microphone which collects ambient sounds of the doctor; and a voice recognition unit 52 which extracts and recognizes specified utterance content regarding the surgical needles (tools) $N_1$ to $N_X$ among the doctor's utterances from the ambient sounds collected via the sound collection unit 51.

The voice recognition unit 52 analyzes voice data indicating the ambient sounds, extracts a voice feature quantity indicating the doctor's utterances and executes voice recognition processing, including morphological analysis, on the content of the utterances, and converts them into text information.

Furthermore, the voice recognition unit 52 is designed to estimate the emotion of the doctor who made the utterances (their emotion of impatience due to the loss of the surgical needle) by using, for example, learning models such as an SVM (Support Vector Machine). The SVM is one of pattern recognition models and can estimate the doctor's emotion by classifying the voice data in accordance with attributes.

Specifically speaking, the SVM prepares a plurality of pieces of utterance content (for example, "Where is the needle?") in advance regarding the surgical needles (tools) $N_1$ to $N_X$ as learning data and classifies the voice data into respective emotions, thereby calculating a threshold value for a specified emotion. Learning models obtained by learning the utterance content regarding the surgical needles $N_1$ to $N_X$ by using the voice data are stored in the reference data storage unit 30.

Then, the voice recognition unit 52 converts the utterance content including the word "needle" in the above-mentioned text information, among the doctor's utterance voice, into a vector whose elements are an utterance speed and an intonation. For example, when the number of seconds required for the utterance is used as the utterance speed and a change in amplitude of the voice is used as the intonation regarding the voice saying, "Where is the needle?," the vector of that voice can be expressed in a form of the number of seconds for the utterance and its spectrum value. The emotion of impatience due to the loss of the surgical needle $N_1$ to $N_X$ is estimated depending on where in a vector space defined by the SVM the vector of this voice is located.

Consequently, the voice recognition unit 52 can extract and recognize the specified utterance content regarding the surgical needle $N_1$ to $N_X$ among the doctor's utterances.

Subsequently, when receiving a recognition result of the utterance content regarding the surgical needle $N_1$ to $N_X$ from the voice recognition unit 52 during a period of time from the first time point to the second time point, the control unit (loss judgment unit) 20 judges that the surgical needle $N_1$ to $N_X$ is lost, even before the second time point passes. As a result, with the needle monitoring apparatus 50, the doctor instantly deals with the loss of the surgical needle $N_1$ to $N_X$ at the time point when the doctor recognizes the loss, so that it is possible to prevent the occurrence of problems attributable to the loss of the surgical needle $N_1$ to $N_X$.

Furthermore, this embodiment has described the case where the movement locus display unit that reads the trace data corresponding to the heads-up time, which is from immediately before the first time point to immediately after the first time point, from the data storage unit (movement locus storage unit) 23 with reference to the corresponding identifier with respect to the surgical needle (tool) $N_K$ judged to have been lost, and displays the movement locus of the tool based on the trace data on the screen is configured from the control unit 20 and the video display unit 4; however, the present invention is not limited to this example and only the video display unit 4 may be equipped with the movement locus display function.

Moreover, the control unit 20 may display the movement locus of the surgical needle (tool) $N_K$, which is judged to have been lost, on the screen by switching to each image capturing unit 3A to 3D on the heads-up time basis. As a result, with the needle monitoring apparatus 1, the doctor (worker) can check in which image capture range by which image capturing unit 3A to 3D the surgical needle (tool) $N_K$ which may highly possibly have been finally lost is included, with respect to each relevant image capturing unit 3A to 3D.

Furthermore, the control unit may display the movement locus of the surgical needle (tool) $N_K$ by the image capturing unit 3A to 3D designated by the doctor (worker) on the screen repeatedly on the heads-up time basis. As a result, with the needle monitoring apparatus 1, the doctor (worker) can visually check the captured image content of the surgical needle (tool) NK, which may highly possibly have been finally lost, many times on the basis of repetitions from immediately before the first time point to immediately after the first time point.

REFERENCE SIGNS LIST 1, 50: needle monitoring apparatus
2: operating table
3A to 3D: image capturing units
4: video display unit
10: needle holder
11: needle counter
20: control unit
21: image processing unit
22: image storage unit
23: data storage unit
25: loss reporting unit
30: reference data storage unit
51: sound collection unit
52: voice recognition unit
$N_1$ to $N_X$: surgical needles
RT1: image recognition processing procedure
RT2: tracking processing procedure

The invention claimed is:

1. A tool monitoring apparatus for monitoring each of a plurality of tools when a worker performs specified work on an object in a workroom and while each tool is sequentially extracted from a tool holder, in which the plurality of tools are retained, until each tool is housed in a tool counter, the tool monitoring apparatus comprising:
a plurality of image capturing units that capture images centered on an area around hands of the worker and the object inside the workroom from multiple directions;
an image recognition unit that recognizes each of the tools, which moves within an image capture range of the plurality of the image capturing units, in the images with respect to each of the image capturing units while assigning an identifier to each of the tools in an order of extraction from the tool holder;
a movement locus storage unit that stores trace data indicating a movement locus of each tool by associating the trace data with the identifier corresponding thereto, while tracking a moving position of each tool for each of the image capturing units with respect to each tool recognized in the images by the image recognition unit;
a loss judgment unit that judges that the tool is lost, at a second time point after an elapse of a certain amount of time or longer after a first time point when it is judged that the tool is not recognized at all in the images by the image recognition unit, with respect to each of the tools regarding which the trace data is stored by the movement locus storage unit; and
a movement locus display unit that displays the movement locus of the tool based on the trace data on a screen, with respect to the tool which is judged by the loss judgment unit to have been lost, by reading the trace data corresponding to heads-up time, which is from immediately before the first time point to immediately after the first time point, from the movement locus storage unit with reference to the corresponding identifier.

2. The tool monitoring apparatus according to claim 1, comprising:
a sound collection unit that collects ambient sounds of the worker; and
a voice recognition unit that extracts and recognizes specified utterance content regarding the tool among utterances of the worker from the ambient sounds collected by the sound collection unit, wherein when the loss judgment unit receives a recognition result of the utterance content regarding the tool from the voice recognition unit during a period of time from the first time point to the second time point, the loss judgment unit judges that the tool is lost, even before the second time point passes.

3. The tool monitoring apparatus according to claim 1, wherein the movement locus display unit displays the movement locus of the tool, which is judged by the loss judgment unit to have been lost, on the screen by switching to each of the image capturing units on the basis of the heads-up time.

4. The tool monitoring apparatus according to claim 1, wherein the movement locus display unit repeatedly displays the movement locus of the tool by the image capturing unit designated by the worker on the basis of the heads-up time.

5. The tool monitoring apparatus according to claim 1, comprising a loss reporting unit that reports a possibility of loss of the relevant tool, by means of either one of, or both, a voice and a light emission, to the worker at the first time point when the loss judgment unit judges that the tool is not recognized at all in the images.

6. The tool monitoring apparatus according to claim 1, wherein when the loss judgment unit judges that, with respect to each of the tools regarding which the trace data is stored by the movement locus storage unit, the tool is not housed in the tool counter after the work is finished, the loss judgment unit judges that the tool is lost.

7. The tool monitoring method according to claim 6, wherein in the third step, a possibility of loss of the relevant tool is reported, by means of either one of, or both, a voice and a light emission, to the worker at the first time point when it is judged that the tool is not recognized at all in the images in the first step.

8. The tool monitoring method according to claim 6, wherein in the third step, when it is judged that, with respect to each of the tools regarding which the trace data is stored by the second step, the tool is not housed in the tool counter after the work is finished, it is judged that the tool is lost.

9. A tool monitoring method for monitoring each of a plurality of tools when a worker performs specified work on an object in a workroom and while each tool is sequentially extracted from a tool holder, in which the plurality of tools are retained, until each tool is housed in a tool counter, the tool monitoring method comprising:
a first step causing a plurality of image capturing units to capture images centered on an area around hands of the worker and the object inside the workroom from multiple directions and recognizing each of the tools, which moves within an image capture range of each of the image capturing units, in the images with respect to each of the image capturing units while assigning an identifier to each of the tools in an order of extraction from the tool holder;

a second step of storing trace data indicating a movement locus of each tool by associating the trace data with the identifier corresponding thereto, while tracking a moving position of each tool for each of the image capturing units with respect to each tool recognized in the images in the first step;

a third step of judging that the tool is lost, at a second time point after an elapse of a certain amount of time or longer after a first time point when it is judged that the tool is not recognized at all in the images in the first step, with respect to each of the tools regarding which the trace data is stored by the second step; and a fourth step of displaying the movement locus of the tool based on the trace data on a screen, with respect to the tool which is judged by the third step to have been lost, by reading the trace data corresponding to heads-up time, which is from immediately before the first time point to immediately after the first time point, with reference to the corresponding identifier.

10. The tool monitoring method according to claim 9, wherein in the third step, when specified utterance content regarding the tool is extracted and recognized among utterances of the worker from ambient sounds of the worker during a period of time from the first time point to the second time point, it is judged that the tool is lost, even before the second time point passes.

11. The tool monitoring method according to claim 9, wherein in the fourth step, the movement locus of the tool, which is judged by the third step to have been lost, on the screen by switching to each of the image capturing units on the basis of the heads-up time.

12. The tool monitoring method according to claim 9, wherein subsequently in the fourth step, the movement locus of the tool by the image capturing unit designated by the worker is displayed repeatedly on the screen on the basis of the heads-up time.

* * * * *